(12) United States Patent
Quintero Martínez et al.

(10) Patent No.: US 12,037,711 B2
(45) Date of Patent: Jul. 16, 2024

(54) METHOD AND DEVICE FOR MAKING CONTINUOUS NANOFIBERS

(71) Applicant: UNIVERSIDADE DE VIGO, Vigo-Pontevedra (ES)

(72) Inventors: Félix Quintero Martínez, Vigo-Pontevedra (ES); Joaquín Penide Durán, Vigo-Pontevedra (ES); Antonio Riveiro Rodríguez, Vigo-Pontevedra (ES); Jesús Del Val García, Vigo-Pontevedra (ES); Rafael Comesaña Piñeiro, Vigo-Pontevedra (ES); Fernando Lusquiños Rodríguez, Vigo-Pontevedra (ES); Juan María Pou Saracho, Vigo-Pontevedra (ES)

(73) Assignee: UNIVERSIDADE DE VIGO, Vigo-Pontevedra (ES)

( * ) Notice: Subject to any disclaimer, the term of this patent is extended or adjusted under 35 U.S.C. 154(b) by 958 days.

(21) Appl. No.: 15/773,945

(22) PCT Filed: Nov. 4, 2016

(86) PCT No.: PCT/ES2016/070776
§ 371 (c)(1),
(2) Date: Oct. 1, 2018

(87) PCT Pub. No.: WO2017/077158
PCT Pub. Date: May 11, 2017

(65) Prior Publication Data
US 2019/0032248 A1 Jan. 31, 2019

(30) Foreign Application Priority Data
Nov. 6, 2015 (ES) ................. ES201531603

(51) Int. Cl.
*D01D 5/098* (2006.01)
*A61F 2/00* (2006.01)
(Continued)

(52) U.S. Cl.
CPC ............. *D01D 5/0985* (2013.01); *A61F 2/00* (2013.01); *A61F 2/0063* (2013.01);
(Continued)

(58) Field of Classification Search
CPC ........ D01D 5/0985; B23K 26/354; A61F 2/00
(Continued)

(56) References Cited

U.S. PATENT DOCUMENTS 5,683,486 A * 11/1997 Oyamada ............... C03B 37/014
65/377
9,243,347 B2 * 1/2016 Joo .......................... D01D 5/14
(Continued)

FOREIGN PATENT DOCUMENTS

| CN | 10 275 665 A | 10/2012 |
| CN | 102 758 264 A | 10/2012 |

(Continued)

OTHER PUBLICATIONS

Machine Translation of JP4876252B2; 2023 (Year: 2023).*
(Continued)

*Primary Examiner* — Nathaniel E Wiehe
*Assistant Examiner* — Thomas J Ward
(74) *Attorney, Agent, or Firm* — Gary J. Gershik (57) ABSTRACT

A device and method for generating long fibers having a nanoscale diameter by combined application of a gas jet and laser radiation. The invention also relates to nanoscale fibers generated by the device and method.

10 Claims, 4 Drawing Sheets

(51) Int. Cl.
| | |
|---|---|
| A61L 27/02 | (2006.01) |
| A61L 27/60 | (2006.01) |
| B23K 26/14 | (2014.01) |
| B23K 26/354 | (2014.01) |
| C08K 7/02 | (2006.01) |
| D01D 5/00 | (2006.01) |
| D01D 5/14 | (2006.01) |
| D01D 13/00 | (2006.01) |

(52) U.S. Cl.
CPC ............ *A61L 27/025* (2013.01); *A61L 27/60* (2013.01); *B23K 26/14* (2013.01); *B23K 26/354* (2015.10); *C08K 7/02* (2013.01); *D01D 5/0023* (2013.01); *D01D 5/0069* (2013.01); *D01D 5/14* (2013.01); *D01D 13/00* (2013.01); *A61F 2240/001* (2013.01); *A61L 2400/12* (2013.01); *A61L 2430/02* (2013.01); *A61L 2430/06* (2013.01); *A61L 2430/34* (2013.01); *Y02P 70/10* (2015.11); *Y02P 70/62* (2015.11)

(58) Field of Classification Search
USPC .................................................. 219/121.85
See application file for complete search history.

(56) References Cited

U.S. PATENT DOCUMENTS

| | | | |
|---|---|---|---|
| 2002/0043091 A1* | 4/2002 | Quick | B21C 37/042 72/342.1 |
| 2010/0148406 A1 | 6/2010 | Suzuki | |
| 2011/0073243 A1 | 3/2011 | Yu et al. | |
| 2015/0240388 A1 | 8/2015 | Joo et al. | |

FOREIGN PATENT DOCUMENTS

| | | | | |
|---|---|---|---|---|
| CN | 103924309 | | 7/2014 | |
| ES | 2 223 290 | | 2/2005 | |
| JP | H04179904 | A | 7/2008 | |
| JP | 2008-179904 | A | 8/2008 | |
| JP | 2010-275665 | | 9/2010 | |
| JP | 4876252 | B2 * | 2/2012 | ............... D01D 5/08 |
| WO | 2011/100743 | A2 | 8/2011 | |

OTHER PUBLICATIONS

Bhardwaj, N. and Kundu, S.C. "Electrospinning: A fascinating fiber fabrication technique", Biotechnology Advances, vol. 28, 2010, pp. 325-347.

Ogata, N. et al., "Poly (lactide) Nanofibers Produced by a Melt-electrospinning System with a Laser Melting Device", Journal of Applied Polymer Science, vol. 104, 2007, pp. 1640-1645.

Quintero, F. et al., "Production of glass nanofibers by a novel technique: Laser Spinning", Laser Spinning, 2010, NanoSpain 2010.

Ramakrishna, S., et al., "Electrospun nanofibers: solving global issues", vol. 9, 2006, pp. 40-50.

Li, Xiuyan, et al., "Preparation and Properties of PET/SiO2 composite Micro/Nanofibres by a Laser Melt-Electrospinning System", Journal of Applied Polymer Science, vol. 125, 2012, pp. 2050-2055.

Zhmayev, E. et al., "Nanofibers from gas-assisted polymer melt electrospinning" Polymer, vol. 51, 2010 pp. 4140-4144.

International Search Report issued by the International Searching Authority (ISA/O.E.P.M.) on Feb. 17, 2017 in connection with International Application No. PCT/ES2016/070776.

* cited by examiner

METHOD AND DEVICE FOR MAKING CONTINUOUS NANOFIBERS

CROSS-REFERENCE TO RELATED APPLICATIONS

This application is a § 371 national stage of PCT International Application No. PCT/ES2016/070776, filed Nov. 4, 2016, claiming priority of Spanish Patent Application P201531603, filed Nov. 6, 2015, the contents of each of which are hereby incorporated by reference into this application.

FIELD OF THE ART

The present invention is comprised in the field of material processing techniques for producing nanomaterials, i.e., materials in which at least one of its dimensions is in nanoscale.

The technique described in the present invention allows producing continuous and separate fibers the diameter of which is in nanoscale and the length of which is indefinitely long.

BACKGROUND OF THE INVENTION

There is an enormous demand for new materials with unique properties that allow introducing significant breakthroughs in various technological fields. This demand motivates the synthesis and application of new nanomaterials that meet these new needs. Out of the different types of nanomaterials that have been investigated, those materials which are almost one-dimensional, such as crystalline nanotubes and nanowires or amorphous nanofibers, are among those which stand out the most. This is because of their remarkable properties resulting from an extraordinarily high ratio of surface area to volume and their reduced diameters. Furthermore, if nanofibers reach a macroscopic length, they can serve as a valuable bridge between macroscopic applications and nanoscale properties, making a beneficial range of applications of the nanomaterials possible.

Nevertheless, the synthesis of nanowires or nanofibers having long lengths and their integration in the sustainable production of functional materials still faces significant challenges. There are a number of industrial methods for obtaining inorganic or polymeric glass fibers with diameters in the microscale range (microfibers). They all involve melting the precursor material so that it can be drawn by means of one of the following three fundamental techniques: 1) rotary fiberizing, which is based on centrifuging the molten precursor through holes made in a drum turning at a high speed; 2) melt blowing, which is based on extruding the precursor material melt through a hole, while a gas jet entrains and cools the filament; 3) mechanical pulling methods, which use different types of mechanical systems to induce axial stress in a molten preform experiencing uniaxial elongation, forming a uniform filament. However, it is not possible to obtain continuous nanofibers having indefinite lengths with any of these methods.

On the other hand, electrospinning is a scalable technique for producing nanofibers with a high productive capacity. It is a simple and efficient technique that allows obtaining nanofibers from a material that must be in liquid state. As a result, it has been used for obtaining polymer nanofibers. However, the production of ceramic nanofibers is very complex with this method due to their high melting point. As a result, sol-gel materials must be used as precursors. However, the results of this method are not always entirely satisfactory: calcination of the sol-gel precursor involves certain drawbacks, as the nanofibers acquire high porosity after the process, which gives them poor mechanical properties. In other cases, the fibers are welded together during the curing and calcination process, which produces a bound web that cannot be separated, ordered, or woven. Furthermore, the incompatibility between some precursor chemical compounds of the sol-gel restricts the range of compositions of the end product.

Alternatively, the laser spinning technique (as disclosed in patent document ES2223290B1) is presented as an effective method for producing amorphous ceramic nanofibers. This technique overcomes the limitations of conventional methods for producing glass fibers, as it allows producing nanofibers having various compositions, including those having a high melting point, as well as those that generate a fragile melt or have a high propensity for devitrification. The nanofibers produced with the "laser spinning" technique have a cylindrical, solid morphology without porosity, separated from one another, such that they can be separated, ordered, and woven. The "laser spinning" technique essentially consists of melting a small volume of a solid precursor by means of a high-power laser, while a supersonic gas jet is injected into the melting area. This gas jet entrains the molten material, causing it to be elongated and cooled in an extremely quick manner, which produces the amorphous nanofibers with the same composition as the precursor material, in large amounts and in a very short time. Nevertheless, this technique also has some limitations: the produced fibers do not all have the same diameter, but rather differ from one another. On the other hand, the lengths of the nanofibers are limited to the centimeter range. Furthermore, the nanofibers that are obtained are mixed with small drops of molten material that must be removed before use.

There is therefore a need in the state of the art for new methods that allow manufacturing solid, continuous, and non-porous fibers having a controlled diameter in the nanoscale range and with indefinitely long lengths.

BRIEF DESCRIPTION OF THE INVENTION

The present invention provides a method for producing solid, continuous, and non-porous fibers with a controlled diameter in the nanoscale range and with indefinitely long lengths. This method is based on the micromelting of a preform made from a precursor material with a high-power laser to generate a microfilament made of molten material. At the same time, a gas jet fed in a coaxial manner with respect to the microfilament at a high speed causes the elongation and cooling thereof.

In a first aspect, the present invention provides a method suitable for producing continuous nanofibers, characterized in that it comprises the following steps:
  a) providing a preform made from a precursor material with an elongated shape and longitudinally moving the preform at a uniform speed toward a processing area,
  b) as the preform made from a precursor material reaches the processing area maintaining a uniform speed, continuously applying laser radiation on the region of the preform that is entering the processing area for heating to a suitable melting temperature, and
  c) continuously applying gas in a coaxial manner with respect to the precursor material melt and in the same direction of movement,
  such that by the combined action of the heating produced by the laser radiation and the coaxial application of the gas, uniaxial drawing of the precursor material melt in the direction of movement takes place in the processing area, its diameter thereby being reduced, and d) as the precursor material melt of reduced diameter exits the processing area, said melt continues to be drawn by the action of the coaxial gas and is cooled, being solidified, until forming a nanofiber.

The advantage of this method compared to the melt blowing method is that in the present invention, the laser beam heating process as well as the gas jet cooling process take place much more quickly than in the melt blowing method. As a result, the heating can be performed up to higher temperatures without the flow breaking due to the effect of instabilities or capillary forces, since the heating and cooling processes are much faster than breaking flows. Performing the method at a higher temperature furthermore involves the advantage of the viscosity of the fluid filament being lower; therefore, elongation takes place very quickly, and the diameter of the preform made from a precursor material can accordingly be reduced by factors of less than $1/1000$. Nanoscale diameters can thereby be attained without the filament breaking or crystallizing.

As regards the laser spinning technique, there are considerable differences in the method of performing it, the experimental configuration, and the results. Firstly, in the laser spinning technique, the precursor material must have a planar and non-elongated plate shape (for example, a cylinder) like in the present invention. In the laser spinning technique, the combined action of the laser beam and the gas jet produce a cut or furrow in a solid plate made of the precursor material. The laser beam strikes the planar plate made of precursor material in a perpendicular manner and the gas jet strikes the plate in an oblique manner, in turn forming a certain angle with the laser beam. In said method, the nanofibers are produced from a small volume of molten material generated in said cut or furrow in the plate made of precursor material. This sometimes entails making little use of the precursor material and a vague control of the diameters of the nanofibers. In contrast, in the method of the present invention, one or more laser beams irradiate an elongated (for example, cylindrical or substantially cylindrical) preform, which is provided with a uniform speed, from one or more directions and in a perpendicular or slightly oblique manner. Meanwhile, the gas jet surrounds the processing area flowing in a coaxial direction with respect to the molten filament. The entire volume of the preform made from a precursor material reaching the processing area is thereby transformed into a nanofiber, so use is made of 100% of the precursor material.

On the other hand, the fibers obtained by means of the laser spinning technique are accompanied by small drops of molten material that must be removed before their practical utilization.

By way of example, a cylindrical preform having a circular section of 600 micrometers in diameter and one meter in length could be transformed into a fiber of 300 nanometers in diameter and $4 \times 10^6$ meters. Furthermore, the method of the present invention allows the precise control of the diameter of the fibers produced by means of suitably selecting the parameters of the precursor material, laser beam heating, and the regime of the coaxial gas jet which causes their cooling and elongation.

In reference to the results, this is the only known technique to date that allows obtaining continuous nanofibers with an indefinitely long length from materials with a high melting point without using precursors that are chemically different from the product. In this sense, it presents a clear advantage with respect to the electrospinning technique, given that materials with a low melting point or chemical precursors in the form of sol-gel must be used in the electrospinning technique. In contrast, in the method object of the present invention, the fibers are obtained directly from a process that involves melting a precursor material with the same chemical composition as the product, so the drawbacks derived from curing and calcining a sol-gel precursor do not arise.

In a second aspect, the invention relates to the nanofibers obtained according to the defined method having a diameter comprised between 1 and 900 nm and a length comprised between 1 cm and $4 \times 10^6$ m. As indicated above, the nanofibers obtained by the method of the present invention are advantageously solid, continuous, and non-porous.

Specifically, the nanofibers obtained by the method of the invention are solid, non-porous, and continuous; furthermore, there are no restrictions as regards the chemical composition of the product on the grounds of incompatibilities of the precursors. Other advantages of the product obtained with the present invention compared to electrospinning is that the obtained fibers are completely separated from one another and are long and flexible, so they can be ordered, aligned, and woven.

In another aspect, the present invention provides a device for producing fibers according to the method of the invention, wherein the devices comprises:

a) a processing head comprising:
  means for housing a preform made from a precursor material with an elongated shape and moving it longitudinally at a uniform speed toward a processing area, and
  means for applying gas in a coaxial manner with respect to the material and in the same direction of movement in the processing area and as it exits same; and b) a set of optical systems suitable for focusing laser radiation on the precursor material as it enters the processing area.

The nanoscale fibers obtained by means of the method object of the present invention can be used for making fire-resistant fabrics, as a polymer reinforcement for manufacturing composites, as a base material for different types of cells in tissue engineering, for bone regeneration, for mucosa regeneration, for skin regeneration, for cartilage regeneration, or for manufacturing active bifunctional and recyclable filters.

DESCRIPTION OF THE DRAWINGS

To complement the description that is being made and for the purpose of helping to better understand the features of the invention, the following drawings are attached as an integral part of said description, in which the fundamental elements of the experimental assembly have been depicted in an illustrative and schematic manner according to different practical examples.

FIG. 2 schematically depicts two plan and elevational views of the configuration of the optical elements required for carrying out the experimental assembly of a device according to an embodiment of the present invention. In the diagram, two laser radiation beams (10) and (11) are aimed at respective total reflection mirrors (12) and (13). The propagation of both beams (16) and (17) is modified by means of respective identical optical instruments (18) and (19) to achieve desired irradiance on the preform (14). The drawing shows the preform emerging from the processing head (15), and the processing area irradiated by the two beams in opposite directions (angle of 180° with respect to one another in the horizontal plane) where transformation of the preform made from the precursor material into a continuous and nanoscale fiber (20) takes place.

DETAILED DESCRIPTION OF THE INVENTION

Method

The present invention provides a method suitable for producing continuous nanofibers with an indefinitely long length, characterized in that it comprises the following steps:
a) providing a preform made from a precursor material with an elongated shape and longitudinally moving the preform at a uniform speed toward a processing area,
b) as the preform made from a precursor material reaches the processing area maintaining a uniform speed, continuously applying laser radiation on the region of the preform that is entering the processing area for heating to a suitable melting temperature, and
c) continuously applying gas in a coaxial manner with respect to the precursor material melt and in the same direction of movement,
such that by the combined action of the heating produced by the laser radiation and the coaxial application of the gas, uniaxial drawing of the precursor material melt in the direction of movement takes place in the processing area, its diameter thereby being reduced, and
d) as the precursor material melt of reduced diameter exits the processing area, said melt continues to be drawn by the action of the coaxial gas and is cooled, being solidified, until forming a nanofiber.

In the context of the present invention, the precursor material is preferably an inorganic glass, a polymer, a ceramic material, a metal, or a metal oxide, the rheological behavior of which varies with temperature, such that when it is heated by laser radiation, it reaches a suitable viscosity to surface tension ratio. In a particular embodiment, the precursor material is selected from the group consisting of silica, phosphate glass, and polymers such as polylactic acid (PLA) or polycaprolactone (PCL). In a more particular embodiment, the precursor material is silica. The optimal viscosity to favor drawing of the preform made from a precursor material to form a nanoscale fiber depends on the properties of each precursor material. Said optimal viscosity must be low enough so as to allow a rapid flow of uniaxial elongation of the preform by the entraining effect caused by the process gas. At the same time, the viscosity must be kept high enough so that the surface tension does not cause the filament to break due to the action of capillary forces.

The precursor material can be in liquid, semi-solid, or solid state. In a preferred embodiment, the precursor material is in solid or semi-solid state. Nevertheless, the precursor material can also be provided in a completely molten state, and it is then considered a liquid.

The precursor material has an elongated shape. In the context of the present invention, "elongated shape" is understood as the stretched out shape in which one dimension is greater than the other two dimensions. Said elongated shape can have, for example, a circular section, triangular section, elliptical section, square section, rectangular section, or any other polygonal section. In a particular embodiment, the preform made from the precursor material has a substantially cylindrical or substantially rectangular prism shape.

In a particular embodiment, the preform made from a precursor material is a cylinder with a circular section having a diameter comprised between about 1 µm and about 10 mm, preferably between about 5 µm and about 5 mm, more preferably between about 10 µm and about 1 mm. In a preferred embodiment, the diameter of the section is comprised between about 100 µm and about 700 µm, preferably between about 200 µm and about 600 µm, more preferably between about 300 µm and about 600 µm. In a preferred embodiment, the preform made from a precursor material is a cylinder with a circular section having a diameter of about 600 µm. In another preferred embodiment, the precursor material is a silica cylinder with a circular section having a diameter of about 600 µm.

The preform made from a precursor material is provided to or fed into the processing area at a uniform speed. In the context of the present invention, uniform speed is understood as a speed that is kept constant throughout the entire process. In a particular embodiment, the uniform speed at which the preform is provided is comprised between about 0.01 and about 100 µm/s, preferably between about 0.1 and about 50 µm/s, more preferably between about 0.5 and about 10 µm/s. In a preferred embodiment, the uniform speed at which the preform is provided is about 1 µm/s.

As the preform made from a precursor material reaches the processing area maintaining a uniform speed, laser radiation is continuously applied on the region of the preform that is entering the processing area for heating to a suitable melting temperature, a microscale melt volume being obtained. In a particular embodiment, the precursor material is melted and/or heated into a microscale volume comprised between 10 and 900 cubic micrometers, preferably into a microscale volume comprised between 100 and 800 cubic micrometers, more preferably between 200 and 600 cubic micrometers, even more preferably between 300 and 500 cubic micrometers.

In a particular embodiment, in step b) of the method of the invention a high-power laser is used to melt and/or raise the temperature of the precursor material. The laser radiation is preferably generated from a laser source selected from Nd:YAG, Nd:glass, Nd:vanadate, Er:YAG, Yb:YAG, Tm:YAG, diode, fiber, disc, $CO_2$, CO, HeCd, copper vapor laser, iodine laser, argon laser, krypton laser, and chemical lasers (HF, DF). The power of the laser source is preferably at least 300 W. In a preferred embodiment, the laser equipment used is a $CO_2$ laser ($\lambda$=10.6 µm) emitting a radiant flux of 950 W.

Figure 1:
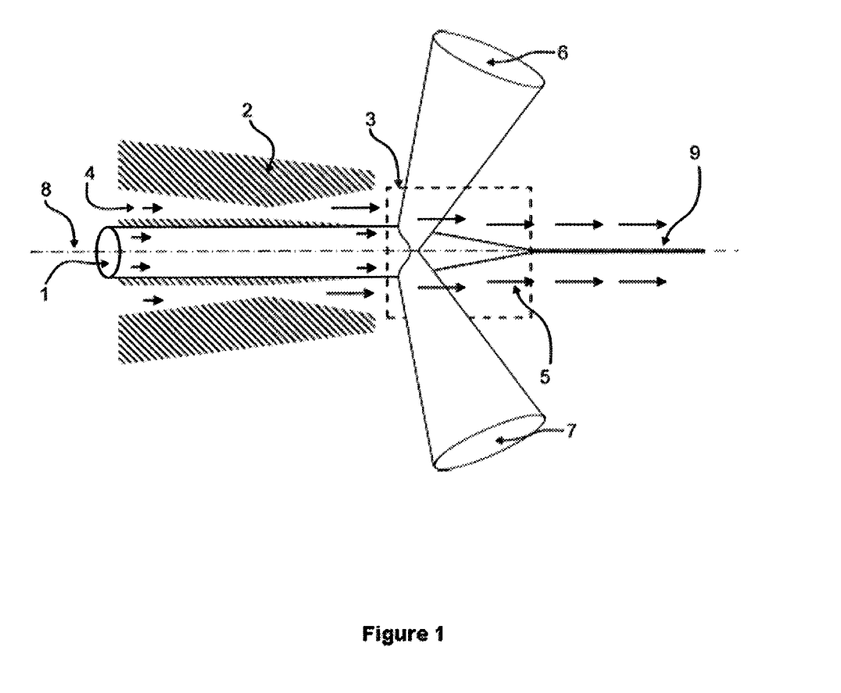
FIG. 1 schematically depicts by way of a cross-section a processing head (2) of a device according to an embodiment of the present invention for injecting gas (4) in a coaxial manner (8) with respect to the flow of precursor material (1). Two laser beams (6 and 7) irradiating the preform made from the precursor material in the processing area (3) from opposite directions, obtaining a microfilament, are also depicted. The reduction of the diameter of the preform in the processing area (5) until producing a continuous nanoscale fiber (9) at the outlet is also schematically shown.
Figure 2:
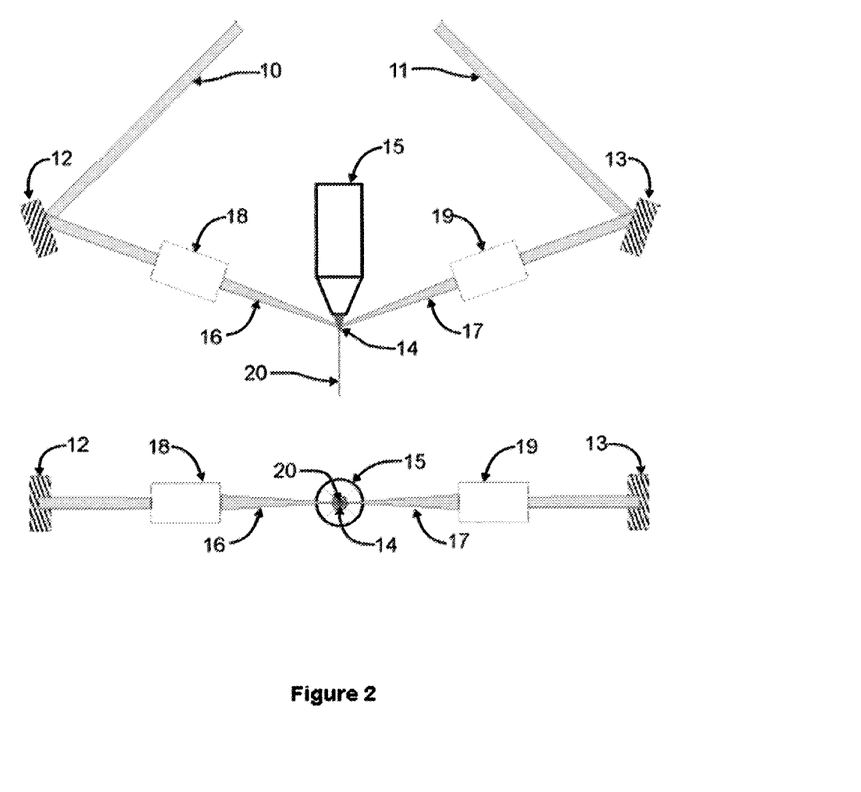

The laser radiation strikes the precursor material from one or more directions so that it can be absorbed into the precursor material in a uniform manner with respect to the axis of symmetry of the precursor material. In a particular embodiment, the laser radiation of step b) comes from two laser beams. The two laser beams are preferably identical. In a preferred embodiment, the two laser beams are facing one another forming an angle of about 180°. More preferably, the laser radiation of step b) of the method comes from two facing identical laser beams forming an angle of about 180°. FIG. 1 schematically depicts a processing head for carrying out the method of the invention where two laser beams irradiate the preform made from the precursor material in the processing area from opposite directions. Likewise, FIG. 2 schematically depicts the processing area being irradiated by two beams in opposite directions.

Figure 3:
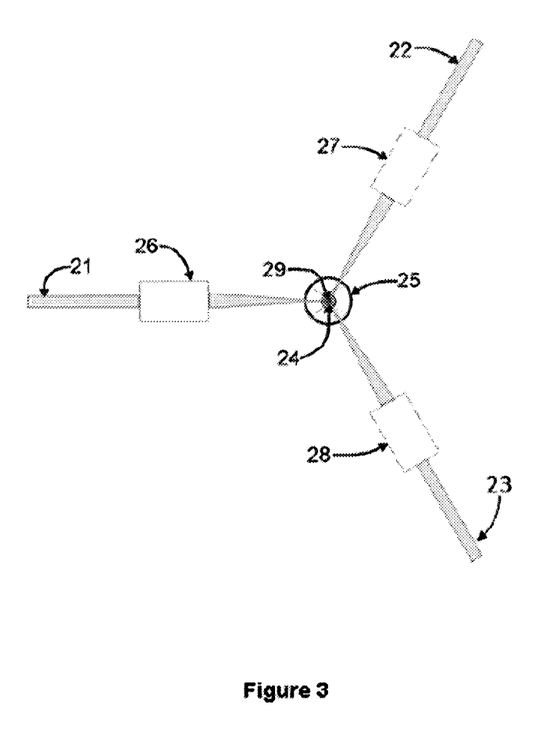
FIG. 3 schematically depicts a plan view of an experimental assembly of a device according to an embodiment of the present invention in which the processing area is irradiated by three identical laser beams (21), (22), and (23). The three beams are aimed at the preform (24) from directions forming an angle of 120° with respect to one another in the horizontal plane. The preform (24) is located concentrically with respect to the processing head (25). The propagation of the three beams (21), (22), and (23) is modified by means of respective identical optical instruments (26), (27), and (28). The preform made from the precursor material is transformed into a continuous and nanoscale fiber (29).

In an alternative embodiment, the laser radiation of step b) comes from three laser beams. The three laser beams are preferably identical. In a preferred embodiment, the three laser beams are located forming an angle of about 120° with respect to one another. More preferably, the laser radiation of step b) comes from three identical laser beams forming an angle of about 120° with respect to one another. FIG. 3 schematically depicts the processing area being irradiated by three identical laser beams.

Figure 4:
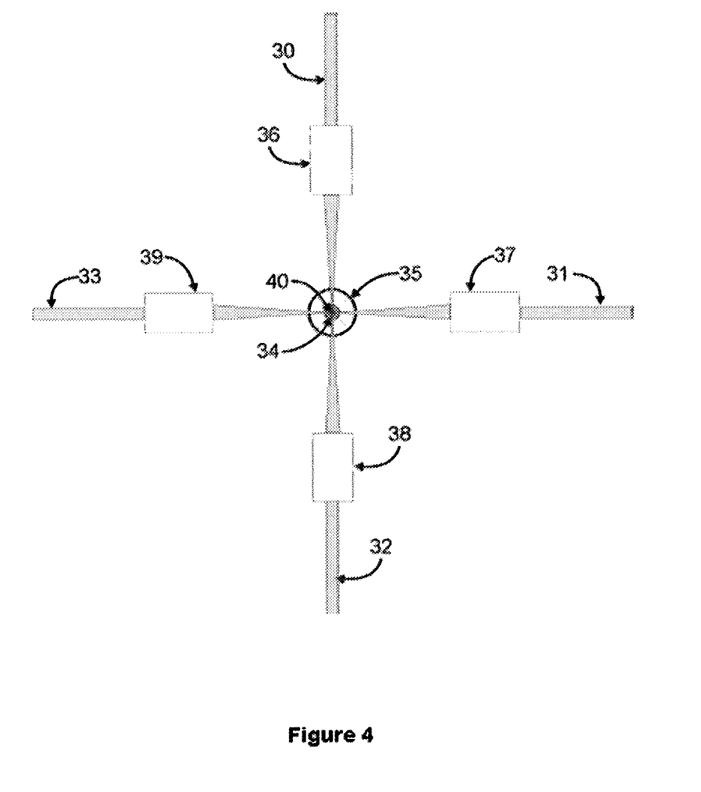
FIG. 4 schematically depicts a plan view of an experimental assembly of a device according to an embodiment of the present invention in which the processing area is irradiated by four identical laser beams (30), (31), (32), and (33) forming an angle of 90° with respect to one another in the horizontal plane. The laser radiations are aimed at the preform (34) which is located concentrically with respect to the processing head (35). The propagation of the four beams (30), (31), (32), and (33) is modified by means of respective identical optical instruments (36), (37), (38), and (39). The preform made from the precursor material is transformed into a continuous and nanoscale fiber (40).

In an alternative embodiment, the laser radiation of step b) comes from four laser beams. The four laser beams are preferably identical. In a preferred embodiment, the four laser beams are located forming an angle of about 90° with respect to one another. More preferably, the laser radiation of step b) comes from four identical laser beams forming an angle of about 90° with respect to one another. FIG. 4 schematically depicts the processing area being irradiated by four identical laser beams.

Absorption of the laser radiation by the precursor material causes the extremely rapid melting of the solid or semi-solid precursor material at a temperature above the melting point or glass transition temperature, or else the heating of the precursor material if it is already in liquid state.

According to step c) of the method of the invention, a gas jet is continuously applied in a coaxial manner with respect to the precursor material melt and in the same direction of movement. The gas jet is coaxially fed at a high speed, which can be supersonic and is conventionally comprised between about 300 and about 900 m/s, such as about 515 m/s, for example, which is equivalent to 1.5 times the speed of sound. In a particular embodiment, the process gas is compressed air, such as compressed air supplied at a gauge pressure of about 300 kPa, for example. The combined action of the heating produced by the laser radiation and the coaxial application of the gas, uniaxial drawing of the precursor material melt in the direction of movement takes place in the processing area, its diameter thereby being reduced until obtaining a microfilament made of the precursor material melt. Additionally, a force can be applied to favor microfilament formation. In the context of the present invention, the force exerted on the precursor material is generally the force of gravity or an external pulling force.

In step d) of the method of the invention, as the microfilament made of molten material obtained in step c) exits the processing area, it continues to be drawn continuously by the action of the coaxial gas that surrounds its entire perimeter. The high-speed gas jet causes rapid elongation, and after the molten material has exited the area of action of the laser radiation, it is cooled and a solid, continuous, and nanoscale-sized fiber is formed. The obtained fiber is cooled by convection of the heat of the high-speed gas flow on the surface of the nanofiber.

In a particular embodiment, the continuous supply of precursor material flow to the processing area, together with the continuous and uniform heating thereof by the laser beam, and the continuous flow of the coaxial gas jet, all in a suitable ratio, establish a stationary regime in the heating, elongation, and cooling process. This stationary regime in the processing area entails the continuous transformation of the preform made from the precursor material into a fiber having a nanoscale diameter with an indefinite length, solely limited by the process duration and speed.

Nanofibers

In another aspect, the invention relates to the nanofiber obtained according to the method of the invention. In a particular embodiment, the nanofiber obtained according to the method of the invention has a nanoscale diameter, for example a diameter comprised between about 1 and about 900 nm, and an "indefinitely long" length, for example a length comprised between about 1 cm and about $4\times10^6$ m. According to particular embodiments, the nanofiber obtained according to the method of the invention has a diameter of from about 1, 50, or 100 nm to about 700, 500, or 300 nm. In a particular embodiment, the diameter is about 300 nm. According to particular embodiments, the nanofiber obtained according to the method of the invention has a length from about 1, 100, or 1000 cm to about 5, 10, 100, or 1000 m. The nanofiber obtained according to the method of the invention preferably has a diameter comprised between about 1 and about 500 nm and a length comprised between about 1 and about 5 m.

The nanofibers obtained by the method of the present invention are advantageously solid, continuous, and non-porous.

Device

The present invention provides a device for carrying out the method of the invention for producing continuous fibers. Therefore, in a particular aspect the invention relates to the device for producing fibers according to the method of the invention, wherein the device comprises:

a) a processing head comprising:
    means for housing a preform made from a precursor material with an elongated shape and moving it longitudinally at a uniform speed toward a processing area, and
    means for applying gas in a coaxial manner with respect to the material and in the same direction of movement in the processing area and as it exits same; and
  b) a set of optical systems suitable for focusing laser radiation on the precursor material as it enters the processing area.

The processing head of the device of the present invention allows housing the precursor material and moving it toward the processing area where laser radiation on the precursor material takes place. Furthermore, the processing head allows injecting the process gas in a coaxial manner with respect to the precursor material flow. In a particular embodiment, the processing head contains an annular conduit through which the process gas flows in a coaxial manner with respect to the microfilament, surrounding it along its entire perimeter. The high-speed gas jet causes rapid elongation and cooling of the molten material, forming a solid, continuous, and nanoscale-sized fiber.

In a particular embodiment, the device of the invention contains a set of optical systems focusing at least one laser radiation on the precursor material, preferably two laser radiations, more preferably three laser radiations. The set of optical systems is preferably formed by mirrors oriented for aiming the laser radiation at the processing area.

The laser radiation can come from any laser equipment generating radiation with a wavelength suitable for being absorbed and transformed into heat in the precursor material and with a large enough emission power to cause the heating of the preform throughout the entire elongation process. The suitable wavelength and operating mode (continuous or pulsed) will be selected depending on the materials to be processed. So in a particular embodiment, the laser radiation in the device of the invention will be continuous or pulsed.

In a particular embodiment, the laser radiation of the device of the invention is selected from Nd:YAG, Nd:glass, Nd:vanadate, Er:YAG, Yb:YAG, Tm:YAG, diode, fiber, disc, $CO_2$, CO, HeCd, copper vapor laser, iodine laser, argon laser, krypton laser, or chemical lasers (HF, DF).

FIG. 1 shows a processing head suitable for the device of the present invention. The precursor material (1) is fed continuously into a conduit inside the processing head (2). The precursor material is supplied in the form of a solid or melted cylinder with a flow rate precisely controlled by means of a feed system that is not described or shown in the diagram. The processing head guides the preform made from the precursor material toward the processing area (3), keeping the coaxial position thereof aligned with the axis of the head (8) and limiting oscillations thereof. At the same time, the process gas is injected from the rear part of the processing head into an annular conduit (4) that is coaxial with the conduit of the precursor material and completely surrounds it. Said conduit is designed to expand the gas until reaching a high flow rate which can be supersonic and forms a jet with low turbulence at the outlet of the processing head (5). The process gas flow is designed to surround the preform in the processing area, producing very rapid entraining and cooling effects due to the effect of high friction and high heat convection of the high-speed gas flow on the surface of the preform.

In a particular embodiment, in the device of the invention the laser radiation comes from two identical laser beams, with the two identical laser beams more preferably arranged facing one another forming an angle of about 180°. The two laser beams (6) and (7) with the same radiant flux and the same distribution of irradiance of the laser radiation in their respective cross-sections preferably strike the preform in the processing area from diametrically opposed directions. Both beams are duly aimed at the preform made from the precursor material to produce a symmetrical distribution of irradiance with respect to the midplane containing the axis (8) and it is transverse to the plane of incidence of both beams. The distribution of irradiance of both beams on the preform is adjusted by means of the set of optical systems of the device of the invention to achieve heating the preform in the processing area. Under the combined action of the heating produced by the two laser beams (6) and (7) and the entraining produced by the coaxial gas jet (5), the preform experiences rapid uniaxial elongation in the direction of the axis (8). Its diameter is thereby reduced continuously in the processing area (3) until generating a continuous nanoscale filament (9). Likewise, the rapid cooling this filament experiences as soon as it exits the area irradiated by the laser beams solidifies the fluid filament, forming a dense and continuous nanoscale fiber.

FIG. 2 shows an example of the assembly of the optical elements required for producing a suitable distribution of irradiance of the laser beams in the processing area to achieve process stability. Two laser radiation beams (10) and (11) with the same wavelength, the same radiant flux, and the same transverse distribution of irradiance are aimed at respective total reflection mirrors (12) and (13). Said mirrors are used to make it easier to align both beams such that they strike the preform made from the precursor material (14) from opposite directions and symmetrically with respect to the axis thereof. This diagram shows the preform emerging from the processing head (15). The propagation of both beams (16) and (17) is modified by means of respective identical optical instruments (18) and (19) to achieve the suitable distribution of irradiance in the processing area. Both optical instruments are made up of a combination of converging and/or diverging, spherical and/or cylindrical lenses located such that the desired distribution of irradiance on the preform (14) is achieved. The heating generated by the absorption of the radiation of the laser beams in the precursor material, combined with the friction and cooling caused by the process gas flow (not depicted in this diagram), produce the transformation of the preform made from the precursor material into a continuous and nanoscale fiber (20).

In a particular embodiment, in the device of the invention the laser radiation comes from three identical laser beams forming an angle of about 120° with respect to one another. As an alternative to the aforementioned configuration, FIG. 3 schematically depicts a plan view of an experimental assembly in which the processing area is irradiated by three identical laser beams. Three laser radiation beams (21), (22), and (23) with the same wavelength, the same radiant flux, and the same transverse distribution of irradiance are aimed at the preform (24) from directions forming an angle of 120° with respect to one another in the horizontal plane, as shown in the drawing. A distribution of irradiance in the cross-section of the preform that is more homogenous than that achieved with the aforementioned configuration of two beams is thereby achieved. This diagram shows the preform being concentric with respect to the processing head (25). The propagation of the three beams (21), (22), and (23) is modified by means of respective identical optical instruments (26), (27), and (28) to achieve the suitable distribution of irradiance in the processing area. Said optical instruments are made up of a combination of converging and/or diverging, spherical and/or cylindrical lenses located such that the desired distribution of irradiance on the preform (24) is achieved. The heating generated by the absorption of the radiation of the laser beams in the precursor material, combined with the friction and cooling caused by the process gas flow (not depicted in this diagram), produce the transformation of the preform made from the precursor material into a continuous and nanoscale fiber (29).

In another particular embodiment, in the device of the invention the laser radiation comes from four identical laser beams forming an angle of about 90° with respect to one another. FIG. 4 schematically depicts a plan view of another alternative configuration in which the processing area is irradiated by four identical laser beams. Four laser radiation beams (30), (31), (32), and (33) with the same wavelength, the same radiant flux, and the same transverse distribution of irradiance are aimed at the preform (34) from directions forming an angle of 90° with respect to one another in the horizontal plane, as shown in the drawing. A distribution of irradiance in the cross-section of the preform that is more homogenous than that achieved with the aforementioned configurations of two and three beams is thereby achieved. This diagram shows the preform being concentric with respect to the processing head (35). The propagation of the four beams (30), (31), (32), and (33) is modified by means of respective identical optical instruments (36), (37), (38), and (39) to achieve the suitable distribution of irradiance in the processing area. Said optical instruments are made up of a combination of converging and/or diverging, spherical and/or cylindrical lenses located such that the desired distribution of irradiance on the preform (34) is achieved. The heating generated by the absorption of the radiation of the laser beams in the precursor material, combined with the friction and cooling caused by the process gas flow (not depicted in this diagram), produce the transformation of the preform made from the precursor material into a continuous and nanoscale fiber (40).

In a particular embodiment, the device further comprises a laser radiation source, preferably two laser radiation sources, more preferably three or four laser radiation sources.

As it is used herein, the term "about" means a slight variation of the specified value, preferably within 10 percent of the specified value. Nevertheless, the term "about" can mean a higher tolerance of the variation depending on the experimental technique used, for example. One skilled in the art understands said variations of a specified value and they are within the context of the present invention. Furthermore, in order to provide a more concise description, some of the quantitative expressions provided herein are not qualified with the term "about". It is understood that whether or not the term "about" is used, the intention is for all the amounts provided herein to refer to the given actual value, and they are also intended to refer to the approximation to such given value that would be reasonably deduced based on the usual experience in the art, including equivalents and approximations due to experimental and/or measurement conditions for such given value.

EXAMPLE

Continuous pure silica nanofibers with an indefinitely long length having a cylindrical cross-section and a uniform diameter of 300 nanometers were produced at a rate of 4 m/s. The precursor material was a cylindrical pure silica preform 600 micrometers in diameter that was fed into the processing area at a rate of 1 µm/s. A processing head with a conduit for the process gas designed to expand said gas until obtaining a supersonic flow of about Mach 1.5 was used. The process gas is compressed air supplied at a gauge pressure of 300 kPa. The laser equipment used was a $CO_2$ laser ($\lambda=10.6$ µm) emitting a beam with a radiant flux of 950 W with a Gaussian distribution of irradiance in continuous mode. Said beam was split into two beams having an identical radiant flux, 475 W each. Each beam was aimed at the processing area by means of respective copper mirrors with an angle of 160° between them (in the vertical plan) on the precursor material inlet side. Before striking the processing area, each beam was transformed by respective identical optical instruments each formed by a spherical lens and another cylindrical lens. Said optical instruments produced a distribution of radiation of each beam in an approximately elliptical section of axes of 30 mm and 2 mm centered on the processing area, such that the direction of the larger side of said ellipse coincided with the direction of the axis of the preform.

Having sufficiently described the nature of the present invention as well as the manner of putting it into practice all that is left to add is that changes to the shape, materials, and arrangement with respect to its assembly and the parts forming can be made provided that said alterations do not substantially change said invention.

What is claimed is:

1. A method for producing a continuous nanofiber without any electrospinning assistance, wherein the method comprises the following steps:
   a) providing a preform made from a precursor material with an elongated shape and longitudinally moving the preform at a uniform speed towards a processing area,
   b) as the preform made from a precursor material reaches the processing area maintaining a uniform speed, continuously applying laser radiation on the region of the preform that is entering the processing area for heating to a suitable melting temperature, and
   c) without applying any electrospinning assistance, continuously applying a gas jet at a speed in a range of 300 m/s to 900 m/s in a coaxial manner with respect to the precursor material melt and in the same direction of movement, such that by the combined action of the heating produced by the laser radiation and the coaxial application of the gas jet without any electrospinning assistance, uniaxial drawing of the precursor material melt in the direction of movement takes place in the processing area, a diameter of the precursor material melt thereby being reduced, and
   d) as the precursor material melt of reduced diameter exits the processing area, said melt continues to be drawn by the action of the coaxial gas jet and is cooled, being solidified, until forming a nanofiber.

2. The method according to claim 1, wherein the laser radiation of step b) comes from two facing identical laser beams forming an angle of about 180° with respect to one another in the horizontal plane.

3. The method according to claim 1, wherein the laser radiation of step b) comes from three identical laser beams forming an angle of about 120° with respect to one another in the horizontal plane.

4. The method according to claim 1, wherein the laser radiation of step b) comes from four identical laser beams forming an angle of about 90° with respect to one another in the horizontal plane.

5. The method according to claim 1, wherein the precursor material is selected from the group consisting of an inorganic glass, a polymer, a ceramic material, a metal, and a metal oxide.

6. The method according to claim 1, wherein the laser source used to generate the laser radiation is Nd: YAG, Nd: glass, Nd: vanadate, Er: YAG, Yb: YAG, Tm: YAG, diode, fiber, disc, $CO_2$, CO, HeCd, copper vapor laser, iodine laser, argon laser, krypton laser, or chemical lasers (HF, DF).

7. The method according to claim 1, wherein the preform precursor material is a silica cylinder with a circular section having a diameter of 600 µm.

8. The method according to claim 1, wherein the speed of movement of the preform toward the processing area is comprised between 0.01 and 100 µm/s.

9. The method according to claim 1, wherein the nanofiber formed in step (d) has a diameter comprised between 1 and 900 nm, and a length comprised between 1 cm and $4\times10^6$ m.

10. The method according to claim 1, wherein the nanofiber formed in step (d) has a diameter comprised between 1 and 500 nm, and a length comprised between 1 and 5 m.

* * * * *